US00H002215H

(19) United States
(12) Statutory Invention Registration
Allen et al.
(10) Reg. No.: US H2215 H
(43) Published: Apr. 1, 2008

(54) ODOR DISCRIMINATION USING BINARY SPIKING NEURAL NETWORK

(75) Inventors: Jacob Allen, Troy, MI (US); Robert L. Ewing, Kettering, OH (US); Hoda S. Abdel-Aty-Zohdy, Rochester Hills, MI (US)

(73) Assignee: The United States of America as represented by the Secretary of the Air Force, Washington, DC (US)

(21) Appl. No.: 10/810,429

(22) Filed: Mar. 29, 2004

(51) Int. Cl.
*G06F 15/18* (2006.01)

(52) U.S. Cl. ..... 706/20
(58) Field of Classification Search ..... 706/1, 706/15, 45; 700/1, 90, 28
See application file for complete search history.

(56) References Cited

U.S. PATENT DOCUMENTS

2003/0144746 A1 * 7/2003 Hsiung et al. ..... 700/28

OTHER PUBLICATIONS

'MOS Fully Analog Reinforcement Neutral Network Chip': Al–Nsour, Abdel–Aty–Zohdy, 2001, IEEE, 0–7803–6685–9, 237–240.*

Japan Patent Publication JP 05–187985, Fumihiro, 1992, Japan Patent Office, detailed description section.*

'Pulsed Neural Networks': Maass, Bishop, 1999, MIT Press, xiii–xix, p. 17–18.*

* cited by examiner

*Primary Examiner*—Daniel Pihulic
(74) *Attorney, Agent, or Firm*—AFMCLO/JAZ; Gina S. Tollefson

(57) ABSTRACT

An odor discrimination method and device for an electronic nose system including olfactory pattern classification based on a binary spiking neural network with the capability to handle many sensor inputs in a noise environment while recognizing a large number of potential odors. The spiking neural networks process a large number of inputs arriving from a chemical sensor array and implemented with efficient use of chip surface area.

13 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ODOR DISCRIMINATION USING BINARY SPIKING NEURAL NETWORK

RIGHTS OF THE GOVERNMENT

The invention described herein may be manufactured and used by or for the Government of the United States for all governmental purposes without the payment of any royalty.

BACKGROUND OF THE INVENTION

The invention relates to electronic nose systems and more specifically to an olfactory classification device.

The mammalian nose has millions of olfactory neurons that are neurologically connected to the olfactory bulb in the brain. Each neuron has a single odor receptor that is stimulated by a specific set of odorants. Odor receptors are not unique, and recent research concludes that the mouse nose, for example, consists of only ~1000 unique odor receptors. Although odor receptors are randomly distributed throughout the nose, common odor receptors unite in a common location of the olfaction bulb. This phenomenon could be responsible for acute sensitivity. Each odor receptor responds to a unique subset of odorants, and each odorant stimulates a unique subset of odor receptors. Each odorant stimulates a unique combination of odor receptors that form a signature, or prototype pattern, for scent.

Currently, electronic nose systems exist, but major problems include size, cost, speed, portability, and ease of use. The problem domain for the electronic nose is twofold. In the first realm, sensitive sensors are necessary to function as transducers that convert chemical signals into the electrical domain. In the second realm, sensor data needs to be processed for scent recognition in a complex environment. The sensor problem is largely solved and is not a focus of this invention. Some of the more successful transducers include metal oxide sensors, ISFET, polymer resonating sensors, and optical bead sensors. However, olfactory pattern recognition and classification remains a challenge, especially in a complex environment with many sensors contaminated by background noise.

Most electronic nose pattern classification techniques use neural networks or statistical data analysis to classify odors. For example, CHEMFET sensors are known to be used for chemical recognition. Prior art shows successfully creating a reinforcement neural network to differentiate between three volatile organic compounds. Genetic algorithms are also being employed with success. Other hybrid approaches also seem promising. Unfortunately, these algorithms require powerful offline computer resources, are limited to about sixteen sensor inputs, are sensitive to noise, must be trained offline, or only detect a small number of odors.

Artificial neural networks have proven to be a useful tool for olfactory pattern recognition; but most silicon-based implementations have been limited in scale due to inherent constraints on chip real estate and synapse routing. The invention presents a new spiking neural network approach to odorant learning and detection based on new learned information about the mammalian olfaction system. The present invention explores a new olfactory pattern classification technique based on a binary spiking neural network. Spiking networks are suited for the olfactory system because they are close approximations to the biological network being emulated. Further, the spiking network of the present invention is ideal for VLSI because it does not require multiplication and uses efficient signal transmission.

SUMMARY OF THE INVENTION

An odor discrimination method and device for an electronic nose system including olfactory pattern classification based on a binary spiking neural network with the capability to handle many sensor inputs in a noise environment while recognizing a large number of potential odors. The spiking neural networks process a large number of inputs arriving from a chemical sensor array and implemented with efficient use of chip surface area.

It is therefore an object of the invention to provide an improved odor discrimination method and device including olfactory pattern classification.

It is another object of the invention to provide an odor discrimination method and device for an electronic nose system including olfactory pattern classification based on a binary spiking neural network with the capability to handle many sensor inputs in a noise environment while recognizing a large number of potential odors.

It is another object of the invention to provide an odor discrimination method and device including a spiking neural network that processes a large number of inputs arriving from a chemical sensor array.

It is another object of the invention to provide an odor discrimination method and device including a spiking neural network that processes a large number of inputs arriving from a chemical sensor array and implemented with efficient use of chip surface area.

These and other objects of the invention are described in the description, claims and accompanying drawings and are achieved by a method of olfactory pattern classification comprising the steps of:

sensing odorants using a plurality of odor receptors;

converting output of said sensing step to binary data;

inputting binary data from said converting step to a spiking neural network;

training said spiking neural network to learn most prevalent combination of odor receptors; and associating said combination of odor receptors from said training step with an output neuron.

DETAILED DESCRIPTION

Artificial neural networks have proven to be a useful tool for olfactory pattern recognition; but most silicon-based implementations have been limited in scale due to inherent constraints on chip real estate and synapse routing. The invention presents a new spiking neural network approach to odorant learning and detection based on new learned information about the mammalian olfaction system. The present invention explores a new olfactory pattern classification technique based on a binary spiking neural network. Spiking networks are suited for the olfactory system because they are close approximations to the biological network being emulated.

Figure 1:
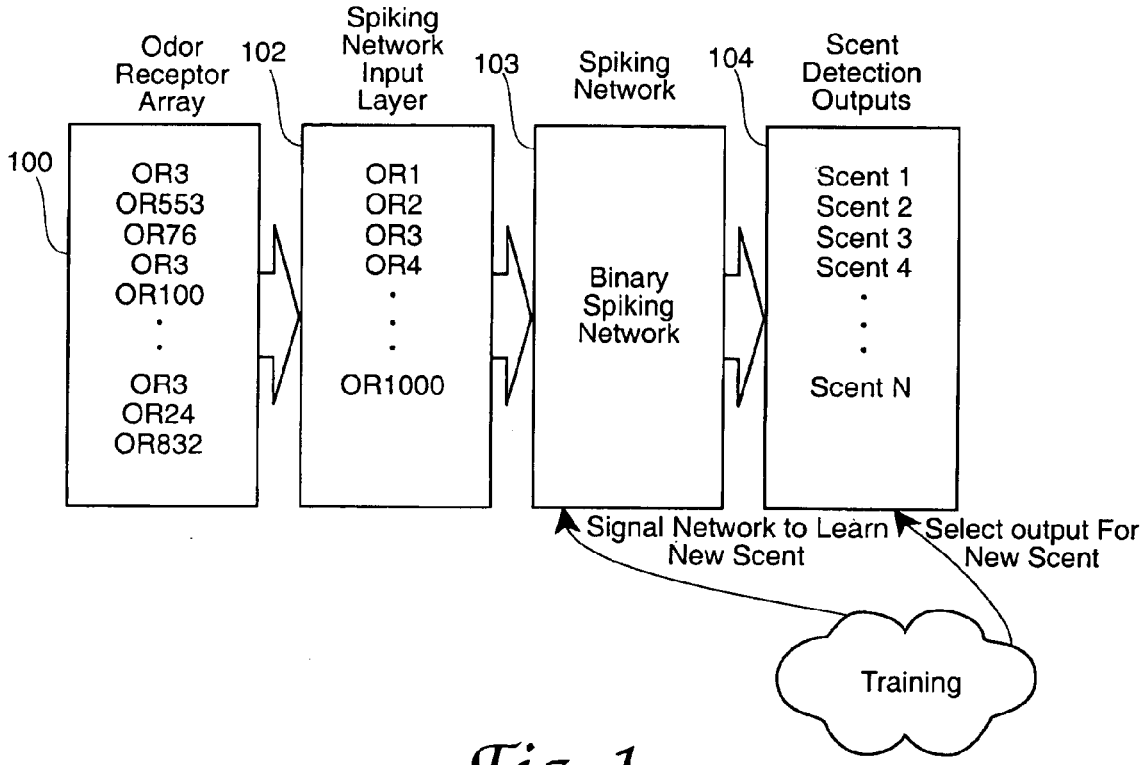
FIG. 1 is a block diagram of the electronic nose arrangement of the invention.

A proposed electronic nose system is diagrammed in FIG. 1. The first layer of the nose at 100, an odor receptor array, is composed of many IONFET sensors, each with one of 1000 different polymers that closely match mammalian odor receptors, that is—sensors with unique polymers for each odor receptor type. A CHEMFET may be used by way of example and other comparable odor receptors may be employed. A CHEMFET sensor is a good replacement for the mammalian odor receptor because the sensor's polymer coating determines which odorants stimulate the sensor. The spiking network input layer at 102 is where the common odor receptors converge at a single point, are averaged, and passed into the spiking network as binary inputs (stimulated/not stimulated) and then fed as an input to the spiking neural network 103. The spiking network 103 and the scent detection output 104 is where the training for the neural network takes place. Thus, the problem domain becomes learning and recognizing binary patterns in 1000 dimensional space. Through the training module, blocks 103 and 104 in FIG. 1, the spiking network can be instructed to learn which combination of odor receptors is most prevalent in the environment and then associate that set with an output neuron. Later, the associated neuron can detect when the learned scent is present. The spiking network handles many parallel inputs and outputs.

During training, illustrated in blocks 103 and 104 in FIG. 1, the system is presented with a scent for about sixty seconds and asked to learn via the training signal. This is similar to the manner in which a bloodhound is presented with the clothing of a missing person to be tracked. The training process assumes that the odor prototype to be learned is more present in the environment than any other prototype. During training, each odor receptor is sampled as a Bernoulli process at a rate of about 10Hz. When training is complete, the inputs that have been the most active are stored in the synapse list of the neuron that has been selected to learn the odor.

Biological neurons receive input spikes via synapses. In the simplest neuron model, each synapse carries a weight that is added to the neuron's internal counter each time the synapse receives a spike. Once the internal counter reaches a certain threshold, the neuron emits a spike and resets the counter. Interestingly, research is proving that synapses have just two states, where one weight represents potentiation and the other weight represents depression.

To test the spiking network, a simulated environment was created to emulate odor receptor inputs to the spiking network. The test stimulus is a time-variant, bit-vector of 1225 values that represents the state of each odor receptor over time. The environment itself is composed of randomly generated odorant prototypes that represent the odor receptors stimulated by a particular odorant. The environment simulates three kinds of noise: (1) background noise is generated to randomly turn on odor receptors; (2) odor receptors in active odorant prototypes are randomly suppressed; and (3) during simulation, distracting prototypes are shuffled in and out of the stimulus space to simulate interference odorants. For this model, NoisePercentOn, NoisePercentOff, and AverageTransitionPenod characterize the noise affecting odor receptors. NoisePercentOn represents the percentage of time that an odor receptor is turned on due to noise. NoisePercentOff represents the percentage of time that an odor receptor is turned off due to noise, and AverageTransitionPeriod represents the average length of time that a sensor is continuously affected by noise.

It should be noted that learning speed is a function of the noise's AverageTransitionPeriod and little else. Because learning is a sampling process, it can be described in terms of precision with statistical confidence intervals. The accuracy of the sampled proportion depends on the number of statistically independent samples taken by the learning unit. The number of statistically independent samples depends on the average transition period of the noise.

In biology, signals are transmitted as spike trains that fluctuate between a low background spike rate and an active maximum spike rate. In this spiking network, binary inputs from odor receptors are converted into similar spike trains, where SpikeRateMin represents the spikes per second generated by a zero input (off), while SpikeRateMax represents an active input (on). This input logic is easy to implement in VLSI as an adder/comparator combination. Each clock cycle, ActivecountAdd is added to InputCounter when the odor receptor is on. Otherwise, the counter increases by one. When the counter reaches CounterThreshold, a spike is posted to the spike bus, and InputCounter resets to 0.

$$InputCounterThreshold := \frac{ClockRate}{SpikeRateMin} \tag{1}$$

$$ActiveCountAdd := \frac{ClockRate}{SpikeRateMinSpikeRateMax}$$

For a compact VLSI implementation, it is necessary to minimize complexity. In this design, the weight of a synapse that is turned on equals one (WeightPotentiated), and the weight of a synapse that is turned off equals zero (WeightDepressed). The neuron itself is just a counter (NeuronStateCounter), a threshold comparator (NeuronStateThreshold), and a variable length list of potentiated synapses. When a spike is received by a potentiated synapse, WeightPotentiated is added to NeuronStateCounter. If NeuronStateCounter reaches NeuronStateThreshold, then the neuron outputs a spike and NeuronStateCounter resets to zero. For this model, the NeuronStateThreshold is always equal to the total number of potentiated inputs.

Figure 2:
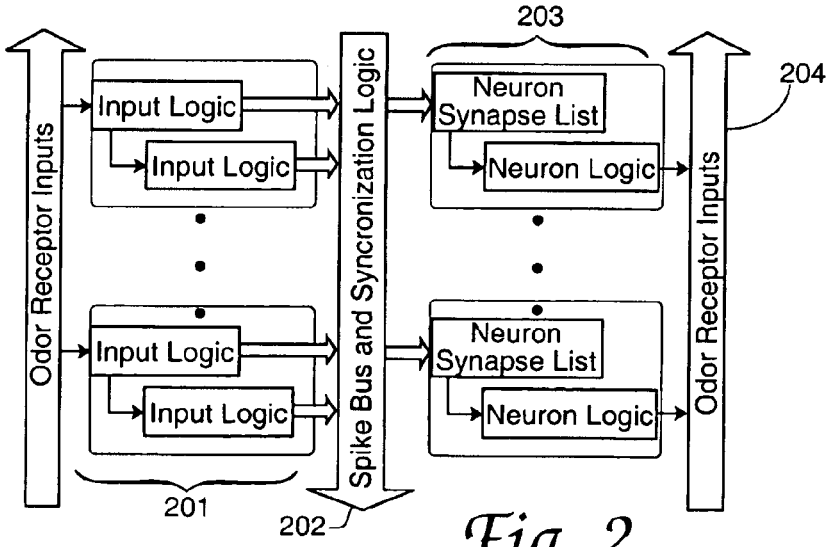
FIG. 2 is a flow diagram showing independent units that combine logic and memory.

FIG. 2 illustrates independent units that combine logic and memory to operate in parallel on a digital bus. The input modules 201 are connected to the neuron modules 203 by the spike bus 202 as shown in FIG. 2. The spike signal from an input is connected to the spike bus 202 using a priority encoder (not shown). The priority encoder posts the address of the input module on the spike bus. The neuron modules 203 are connected in parallel to the spike bus 202 by their potentiated synapse list. Neurons listen for spikes on the spike bus 202, and the number of listening output neurons can be unlimited. To minimize the logic circuit, the learning mechanism was moved from the neuron module to the input module. This works because only one neuron will undergo training at any given time, plus it has the advantage that a neuron can learn from any input in the system. It should be noted that the clock used to communicate spikes on the bus is much faster than the processing clock, so the number of allowed inputs can scale to a very large number.

Mathematically, the binary spiking neuron acts as an averaging function, where the output spike rate of a neuron is just the average spike rate of its potentiated inputs.

$$OutputSpikeRate = \frac{\sum_{SynapseIndex=1}^{SynapseCount} InputRate_{SynapseIndex}}{SynapseCount} \tag{3}$$

Now consider a neuron that has perfectly learned an odor prototype. In this case, the synapse list exactly matches the odor receptor signature of the prototype. For this neuron, the OutputSpikeRate will be exactly proportional to the number of inputs in the prototype that are turned on (PrototypePercentOn).

$$OutputSpikeRate = SpikeRateMin + PrototypePercentOn(SpikeRateMax - SpikeRateMin) \tag{4}$$

Thus, the neuron spike rate is proportional to the PrototypePercentOn, which can be viewed as a hamming distance between a prototype odor and the environmental input space. Finally, we define PrototypePercentOn acceptable to detect an active prototype. From this, we can easily establish a detection threshold for a prototype based on the output spike rate.

$$\text{HammingDistance}=\text{PrototypeSize}-\text{PrototypePercentOn}*\text{PrototypeSize} \quad (5)$$

$$\text{OutputSpikeRateThreshold}=\text{SpikeRateMin}+(\text{SpikeRateMax}-\text{SpikeRateMin})*\text{PrototypPercentThreshold} \quad (6)$$

Background noise, or NoisePercentOn, will artificially inflate. OutputSpikeRate and could result in erroneous detections. However, with the addition of another counter and comparator, we can effectively measure the network's average NoisePercentOn and cancel it. Suppose that a neuron spikes at a rate of BackgroundOutputRate due to noise. The excess output rate can be measured as:

$$(\text{BackgroundOutputRate}-\text{SpikeRateMin})\ \text{N}=\text{OutputRateError} \quad (7)$$

However, by adding inhibitory logic to the neuron circuitry, we can subtract OutputRateError from the OutputSpikeRate and increase the neuron's tolerance to noise.

Figure 3:
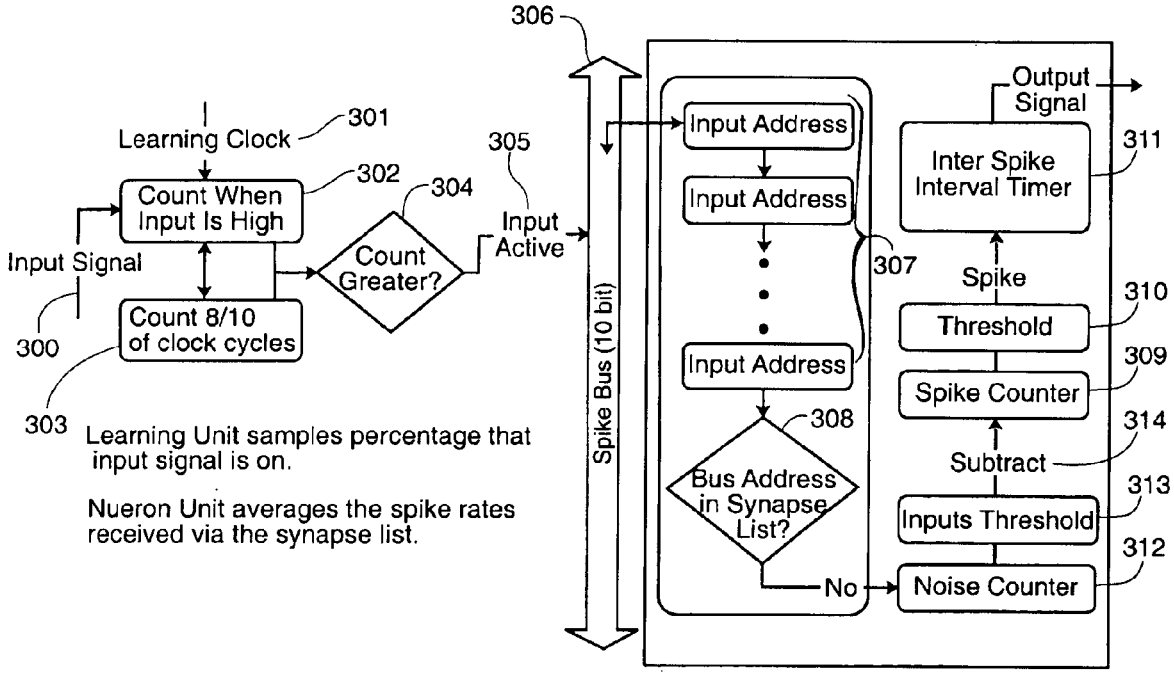
FIG. 3 is a flow diagram showing learning and detection.

FIG. 3 is a flow diagram showing learning and detection of an odor. The left side of the flow chart of FIG. 3 shows learning samples 300 taken on the rising edge of the learning clock 301. Each input has a sample counter 302. If the input is on when a sample is taken, the sample counter is incremented (this happens in parallel for each input). A global counter 303 increments 4 out of every 5 learning clock rising edges (which is, 8 out of 10). At the end of learning, 304, every input's sample counter, 302, is compared to the global counter, 303. If the sample counter 302 is greater than the global counter 303, then the input was on for at least 80% of the samples. This effectively tests for a sampling proportion of 80% during learning. Any input that was on during 80% of the learning samples is "learned", and stored in the neuron's address list.

The right hand side of the flow graph of FIG. 3 shows detection, that is, a neuron listening to the spike bus. An input 305 communicates a spike by placing its input address 307 on the spike bus 306. The neuron has a list of address 308 which were learned using the left side of the flow graph of FIG. 3. Each spike on the spike bus is compared with the address list. (This comparison happens in parallel for all neurons.) When a spike address is in the address list, the Spike Counter 309 is incremented. Once the Spike Counter reaches a threshold 310, the neuron emits a spike and resets the Spike Counter to 0. The threshold is equal/proportional to the number of addresses stored in the address list. The time between neuron spikes is measured at 311. When the time between spikes is below a certain timing threshold, the neuron is considered 'on'. When a neuron is 'on', it is detecting the odor that it learned. Conversely, when the time between spikes is above a certain threshold, the neuron is considered 'off', and the odor learned by the neuron is not present. When a spike address is not in the address list, Noise Counter 312 is incremented. When the Noise Counter 312 reaches a threshold 313, an amount is subtracted 314 from the Spike Counter. Also, the Noise Counter 312 resets to 0. This subtraction step is effectively inhibition. Subtraction makes it less likely that the neuron will fire before the timing threshold, and makes it more likely that a neuron will be 'off'. This step helps to cancel the effect of noise in creating false detections.

The target odor environment is at least 1023 inputs, to approximate the number of odor receptors in the mammillae nose, thus the defined size of the spike bus, illustrated at 306 in FIG. 3, is 10 bits wide, plus another bit for the BusClock signal. Each input corresponds to an odor receptor. Once the spike bus is defined, the system needs a component to convert binary inputs into spike trains. The 11th bit of the spike bus is the 'Save Address' bit, and it signals to the synapse when an input should be saved. A synapse only responds to the 'Save Address' bit of the spike bus when (a) it is not already loaded with an address and (b) when it is enabled. A synapse is only enabled when the odor to which it belongs is selected. Only one synapse can ever be selected. Further, a synapse is only enabled when the synapse before it is loaded. The net result is that one, and only one synapse ever responds to the Save Address bit. When the odor receptor is active, the input is active. When the input is active, it spikes at a rate von, and when the input is inactive, it spikes at a rate voff . Therefore, we define a synchronous spike bus that operates at a specified frequency, fspikebus. Inputs communicate spikes by posting their address, or identification number, on the spike bus. The address is only valid during the rising edge of the BusClock signal. For example, the input corresponding to OR4 would post a binary 4 on the spike bus. The spike bus is defined to be inactive when the address posted is 0. Now that the spike bus is defined, the system needs a component to convert binary inputs into spike trains. Inputs to the network dynamically change state due to noise and fluctuations in the odorant environment, represented by the Noisecounter block at 312 in FIG. 3, and the "No" logic branch decision in the block for the detection mode. If the Bus Addressed in the Synapse is "true", for the logic branch of the detection mode the Spike counter 309, increases each time that a spike is received. Once the Spike counter 309 reaches a present threshold level 310, the Spike counter 309 is reset to zero, and a decision is made about whether the neuron is active or inactive. The decision is based on the inter-spike-interval, InterSpikeIntervalCounter, which is the time period that it took the Spikecounter to increment from 0 to threshold level. The InterSpikeIntervalCounter directly proportional to the percentage of the neuron's learned inputs that are stimulated, which becomes the output signal.

The binary spiking network has been simulated in an environment with 1225 inputs and 50 prototypes, where each prototype is composed on 100 randomly selected inputs. Noise in the environment is generated by three sources. Typically, 10% of the inputs are randomly turned on at any given time to simulate background noise. When a prototype is present, 10% of its inputs are randomly turned off to imitate detection noise. Finally, 10 prototypes are randomly present in the environment at any given time to represent distracting stimuli. In this simulated environment, detection and learning functioned as according to theory, even in an extremely noisy stimulus space.

The present invention is an overview of how spiking neural networks, CHEMFET technology, and new research in mammalian olfaction can be combined to solve odor discrimination challenges that exist for a single chip electronic nose. The invention advances biochemical detection research with a number of unique contributions. First, we have demonstrated that spiking networks can process a large number of inputs arriving from a chemical sensor array and still be implemented with low gate counts and efficient use of chip surface area. Additionally, the network modules combine memory and processing into independent cells that allow for nearly unlimited parallel detection of odor prototypes. Further, the system includes online learning so there is no need for offline training. Finally, simulation shows that the algorithms for learning and detection function well in the presence of noise.

While the apparatus and method herein described constitute a preferred embodiment of the invention, it is to be understood that the invention is not limited to this precise form of apparatus or method and that changes may be made therein without departing from the scope of the invention which is defined in the appended claims.

What is claimed is:

1. A method of olfactory pattern classification comprising the steps of:

sensing odorants using a plurality of odor receptors;

converting output of said sensing step to binary data;

inputting binary data from said converting step to a spiking neural network;

training said spiking neural network to learn most prevalent combination of odor receptors; and associating said combination of odor receptors from said training step with an output neuron.

2. The method of olfactory pattern classification of claim 1 further comprising the step of converting said binary data into spike trains comprising an adder/comparator combination having an input of zero representing a lack of odorant stimulus and an input of one representing an odorant stimulus.

3. The method of olfactory pattern classification of claim 2 wherein said training step further comprises the steps of:

summing active inputs to a counter for every clock cycle of said adder/comparator combination;

adding one to every clock cycle of said adder/comparator for every zero input;

posting a spike to a spike bus every time said counter reaches a specified threshold; and resetting said counter to zero after said posting step.

4. The method of olfactory pattern classification of claim 3 wherein said summing step further comprises summing active inputs to a counter for every 20 KHz clock cycle of said adder/comparator combination.

5. The method of olfactory pattern classification of claim 1 wherein said sensing step further comprises sensing odorants using a plurality of CHEMFET odor receptors.

6. The method of olfactory pattern classification of claim 1 wherein said sensing step further comprises sensing odorants using a plurality of IONFET odor receptors.

7. The method of olfactory pattern classification of claim 1 wherein said training step further comprises the steps of:

receiving an input signal from an olfactory receptor;

summing said input from said receiving step;

adding one to a clock cycle for every input signal from said receiving step;

comparing values from said summing step and said adding step and comparing to a preselected threshold value;

inputting an above threshold value from said summing step to a spike bus;

determining whether value from said inputting step matches data on a synapse listing;

adding values from said determining step that do not match data on said synapse listing to a noise counter;

adding values from said determining step that do match data on said synapse list to a spike counter; and outputting a signal associated with said spike counter after inputs to said spike counter reach a preselected threshold value.

8. The method of olfactory pattern classification of claim 7 wherein said inputting step further comprises the steps of:

providing a spike bus including synchronization logic;

connecting input signal from said receiving step to said spike bus using a priority encoder;

posting address of said input signal on said spike bus using said priority encoder; and connecting neuron modules in parallel to said spike bus by a potentiated synapse list.

9. The method of olfactory pattern classification of claim 7 wherein said determining step further comprises the step of determining whether value from said inputting step matches data on a synapse listing containing odor receptor signatures.

10. A method of olfactory pattern classification comprising the steps of:

sensing odorants using a plurality of odor receptors;

first converting output of said sensing step to binary data;

second converting said binary data into spike trains comprising an adder/comparator combination having an input of zero representing a lack of odorant stimulus and an input of one representing an odorant stimulus;

summing active inputs to a counter for every clock cycle of said adder/comparator combination;

adding one to every clock cycle of said adder/comparator for every zero input;

posting a spike to a spike bus every time said counter reaches a specified threshold;

resetting said counter to zero after said posting step;

training said spiking neural network to learn which combination of odor receptors is most prevelant; and associating a set of most prevelant ordor receptors with an output neuron.

11. An olfactory pattern classification device comprising:

a plurality of odor receptors for sensing odorants;

means for converting output of said odor receptors to binary data;

a spiking neural network for receiving said binary data comprising:

a plurality of potentiated synapses, wherein the weight of an off synapse is zero and the weight of an on synapse is one;

a counter for adding positive weights from said potentiated synapses;

a threshold comparator for determining when said counter has reached a preselected threshold value;

a training program for training said spiking neural network to learn which combination of odor receptors is most prevelant; and a specified output neuron specified by which set of odor receptors are most prevelant.

12. The olfactory pattern classification device of claim 11 wherein said training program further comprises:

a spike bus providing synchronization logic;

a priority encoder for connecting an input signal from said spike bus and for posting address of said input signal on said spike bus; and a potentiated synapse list for connecting neuron modules in parallel to said spike bus.

13. The olfactory pattern classification device of claim 12 wherein said potentiated synapse list further comprises a potentiated synapse list comprising odor receptor signatures.

* * * * *